United States Patent
Savoia

(10) Patent No.: US 7,014,463 B2
(45) Date of Patent: Mar. 21, 2006

(54) DENTAL HYGIENE ACCESSORY

(76) Inventor: Dominic Savoia, 221 Rykert Street, St. Catharines, Ontario (CA) L2S 2B5

(*) Notice: Subject to any disclaimer, the term of this patent is extended or adjusted under 35 U.S.C. 154(b) by 0 days.

(21) Appl. No.: 10/885,689

(22) Filed: Jul. 8, 2004

(65) Prior Publication Data

US 2005/0032023 A1    Feb. 10, 2005

Related U.S. Application Data

(60) Provisional application No. 60/489,479, filed on Jul. 24, 2003.

(51) Int. Cl.
*A61C 3/00*    (2006.01)

(52) U.S. Cl. .................. 433/141; 433/163; 433/229
(58) Field of Classification Search ............... 433/141, 433/229, 163, 49; 15/106, 107, 111, 114, 15/229.11, 167.1, 299.11, 112, 105.52, 21.1, 15/22.1; 206/63.5; 224/217
See application file for complete search history.

(56) References Cited

U.S. PATENT DOCUMENTS

| | | | | |
|---|---|---|---|---|
| 1,993,662 A | * | 3/1935 | Green | 15/167.1 |
| 4,679,274 A | * | 7/1987 | Friedman | 15/167.1 |
| 5,368,482 A | * | 11/1994 | Johnsen et al. | 433/163 |
| 6,116,252 A | * | 9/2000 | Stelmach | 132/309 |
| 6,257,888 B1 | * | 7/2001 | Barham | 433/163 |

* cited by examiner

*Primary Examiner*—Cary E. O'Connor
*Assistant Examiner*—Patrick J. Kilkenny
(74) *Attorney, Agent, or Firm*—Robert F. Delbridge

(57) ABSTRACT

A dental hygiene accessory for cleaning a dental scaler or similar dental instrument has a platform member with a multitude of bristles upstanding from a central area of the platform. An annular body of soft dental debris retaining material is carried by the platform and surrounds the bristles. The accessory also has a retainer extending downwardly from the platform and engageable with a hygienist's finger to retain the accessory thereon.

2 Claims, 2 Drawing Sheets

DENTAL HYGIENE ACCESSORY

RELATED APPLICATION

This application claims priority from U.S. provisional patent application No. 60/489479 filed Jul. 24, 2003.

FIELD OF INVENTION

This invention relates to dental hygiene accessories which are used by a hygienist when cleaning a patient's teeth, and in particular when removing debris therefrom by means of a dental scaler or similar dental instrument.

BACKGROUND OF INVENTION

When working on a patient's teeth, a hygienist has to stand or sit in a suitable position relative to the patient. From time to time, when using a dental scaler, the hygienist has to remove debris from the scaler. This is usually done by using a wad of sterile gauze held in the opposite hand holding the scaler or located on an adjacent tray. This may result in cuts or abrasions to the hand holding the gauze.

It is therefore an object of the present invention to provide a dental hygiene accessory which overcomes the problem mentioned above.

SUMMARY OF INVENTION

According to the invention, a dental hygiene assessory for cleaning a dental scaler or similar dental instrument has a platform member, a multitude of bristles upstanding from a central area of the platform and an annular body of soft dental debris retaining material carried by the platform and surrounding the bristles, the assessory also having a retainer extending downwardly from the platform and engageable with a hygienist's finger to retain the assessory thereon.

Thus, a hygienist can hold a dental scaler in one hand and mount the assessory on the finger of the other hand so that the scaler can easily be cleaned by pulling it through the bristles and/or wiping it on the soft material.

The assessory may have an annular wall upstanding from the central area of the platform member, with the bristles being located within and projecting above the annular wall and the annular body of debris retaining material surrounding the annular wall.

BRIEF DESCRIPTION OF THE DRAWINGS

One embodiment of the invention will now be described, by way of example, with reference to the accompanying drawings, of which.

DESCRIPTION OF PREFERRED EMBODIMENT

Figure 1:
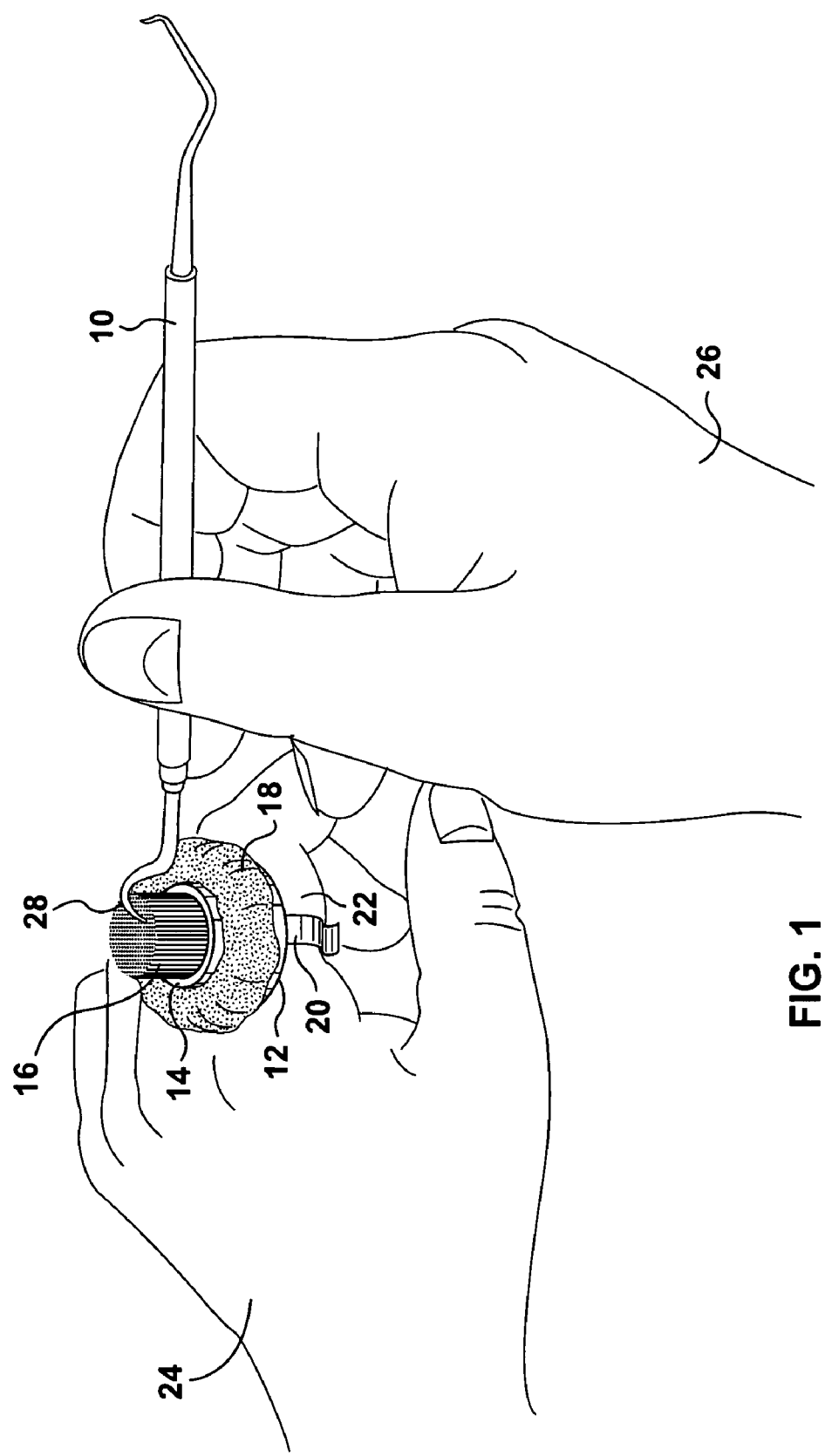
FIG. 1 is a perspective view of a dental hygiene assessory in accordance with one embodiment of the invention mounted on the forefinger of one hand for cleaning a dental scaler held in the other hand of a hygienist.
Figure 2:
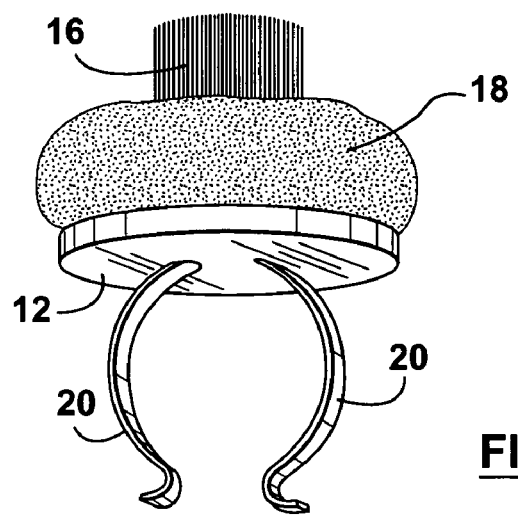
FIG. 2 is a perspective side view of the dental hygiene assessory.
Figure 3:
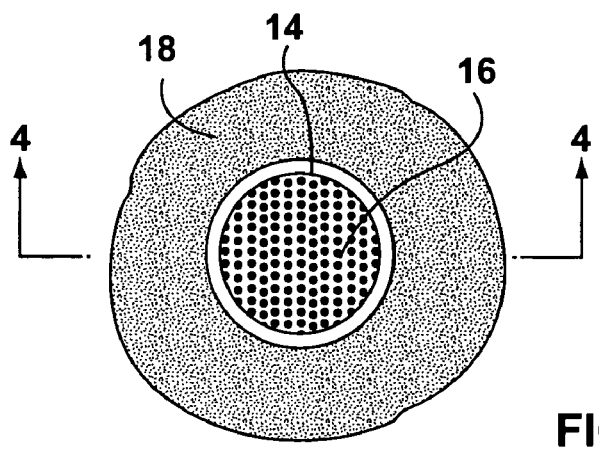
FIG. 3 is a plan view thereof.
Figure 4:
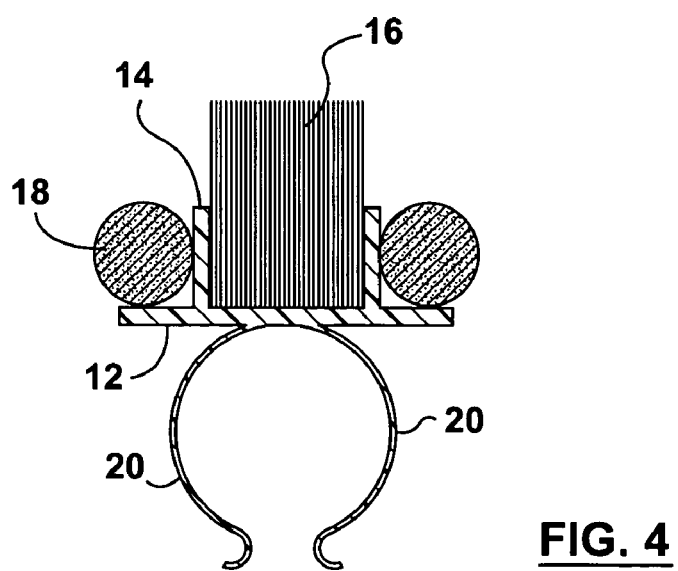
FIG. 4 is a sectional side view thereof taken along the line 4—4 of FIG. 3.

Referring to the drawings, a dental hygiene assessory for cleaning a dental scaler 10 has a circular disk-like platform member 12 with an annular wall 14 upstanding from a central area thereof. A multitude of bristles 16 are secured within the annular wall 14 by a suitable adhesive and project upwardly therefrom. An annular body 18 of soft dental debris retaining material surrounds the annular wall 14 and bristles 16 and is secured to the platform member 12 by a suitable adhesive. The debris retaining material may for example be absorbent cotton material.

The dental assessory also has a retainer formed by a pair of oppositely disposed and spaced curved arms 20 which extend downwardly from the platform member 12 for mounting on a forefinger 22 of one hand 24 of a hygienist.

In use, as shown in FIG. 1, the hygienist will hold the scaler 10 in the other hand 16 and clean a debris carrying end 28 of the scaler in the bristles 16 and/or the soft debris retaining material 18.

The improved safety and convenience afforded by a dental hygiene assessory in accordance with the present invention will now be readily apparent to a person skilled in the art from the foregoing description of a preferred embodiment. Other embodiments of the invention will also now be readily apparent to a person skilled in the art, the scope of the invention being defined by the appended claims.

I claim:

1. A dental hygiene accessory for cleaning a dental scaler or similar dental instrument having a platform member, a multitude of bristles upstanding from a central area of the platform and an annular body of soft dental debris retaining material carried by the platform and surrounding the bristles, said debris retaining material comprising absorbent cotton material, the accessory also having a retainer extending downwardly from the platform and mountable on a hygienist's finger to retain the accessory thereon.

2. A dental hygiene accessory according to claim 1 also having an annular wall upstanding from the central area of the platform member, with the bristles being located within and projecting above the annular wall and the annular body of debris retaining material surrounding the annular wall.

* * * * *